US009788792B2

United States Patent
Goldish et al.

(10) Patent No.: US 9,788,792 B2
(45) Date of Patent: *Oct. 17, 2017

(54) SYSTEM FOR SCREENING SKIN CONDITION FOR TISSUE DAMAGE

(71) Applicants: The United States of America, as Represented by the Department of Veterans Affairs, Washington, DC (US); The Regents of the University of Minnesota, St. Paul, MN (US)

(72) Inventors: Gary D. Goldish, Plymouth, MN (US); Andrew Hansen, Apple Valley, MN (US); Eric Nickel, Chicago, IL (US); John E. Ferguson, Eagan, MN (US)

(73) Assignee: The United States of America, as represented by Department of Veterans Affairs, Office of General Counsel, Professional Staff Group IV(024), Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/061,085

(22) Filed: Mar. 4, 2016

(65) Prior Publication Data

US 2016/0183879 A1    Jun. 30, 2016

Related U.S. Application Data

(63) Continuation-in-part of application No. 13/644,045, filed on Oct. 3, 2012, now Pat. No. 9,301,688.
(Continued)

(51) Int. Cl.
G03B 29/00   (2006.01)
G03B 41/00   (2006.01)
(Continued)

(52) U.S. Cl.
CPC ............ *A61B 5/702* (2013.01); *A61B 5/0077* (2013.01); *A61B 5/0082* (2013.01); *A61B 5/015* (2013.01);
(Continued)

(58) Field of Classification Search
USPC .............................................. 396/14; 600/592
See application file for complete search history.

(56) References Cited

U.S. PATENT DOCUMENTS 4,534,365 A * 8/1985 Bonetta .................. A61B 5/015 108/23
5,168,634 A * 12/1992 Misevich ............. A61B 5/1036 33/512
(Continued)

FOREIGN PATENT DOCUMENTS

WO    2004002309 A1    1/2004

OTHER PUBLICATIONS

Armstrong, D., et al. "Skin Temperature Monitoring Reduces the Risk for Diabetic Foot Ulceration in High-risk Patients", American Journal of Medicine, v. 120, pp. 1042-1046.

Primary Examiner — Clayton E Laballe
Assistant Examiner — Warren K Fenwick
(74) Attorney, Agent, or Firm — Robert Gorman; Gorman Law Offices

(57) ABSTRACT

The present invention relates to a novel approach means of screening various skin surfaces, including hard to reach areas of the human body, as well as more commonly seen areas such as the foot. The present invention can help patients, especially those who are immobile or those with diabetes self-monitor and transmit the skin condition accurately, so that medical providers may assess the risk or presence of skin tissue breakdown. Thus, provision is made for a remote screening device that can be used in telemedi-
(Continued)

cine or home self-monitoring approaches and offers high resolution image, without artifacts or other distortions that might arise from images taken of feet that have been compressed through standing and the like.

12 Claims, 12 Drawing Sheets

Related U.S. Application Data

(60) Provisional application No. 61/551,589, filed on Oct. 26, 2011.

(51) Int. Cl.
*A61B 5/00* (2006.01)
*A61B 5/01* (2006.01)

(52) U.S. Cl.
CPC ............ *A61B 5/447* (2013.01); *A61B 5/6829* (2013.01); *A61B 5/70* (2013.01); *A61B 5/004* (2013.01); *A61B 5/0075* (2013.01); *A61B 5/445* (2013.01); *A61B 2576/02* (2013.01)

(56) References Cited

U.S. PATENT DOCUMENTS

| | | | | |
|---|---|---|---|---|
| 5,790,256 A * | 8/1998 | Brown | ............. | A43D 1/02 33/3 R |
| 5,941,835 A * | 8/1999 | Sundman | ............. | A61B 5/1036 600/592 |
| 5,944,676 A * | 8/1999 | Grassi | ............. | A43D 1/025 600/592 |
| 6,030,351 A * | 2/2000 | Schmidt | ............. | A61B 5/1036 600/592 |
| 6,113,264 A * | 9/2000 | Watanabe | ............. | A61B 6/4441 378/196 |
| 6,200,024 B1 * | 3/2001 | Negrelli | ............. | A61B 6/4233 378/196 |
| 6,289,107 B1 * | 9/2001 | Borchers | ............. | A43D 1/02 356/391 |
| 7,976,482 B2 * | 7/2011 | Mayr | ............. | A61B 5/1071 600/592 |
| 8,192,375 B2 * | 6/2012 | Boneh | ............. | A43D 1/025 600/587 |
| 8,240,769 B1 * | 8/2012 | Story | ............. | A47C 16/00 297/423.1 |
| 8,351,770 B2 * | 1/2013 | DePaula | ............. | G03B 15/00 396/14 |
| 8,638,364 B2 * | 1/2014 | Chen | ............. | G01S 11/12 348/135 |
| 9,301,688 B2 * | 4/2016 | Goldish | ............. | A61B 5/0077 |
| 2004/0168329 A1 | 9/2004 | Ishimaru | | |
| 2006/0201011 A1 * | 9/2006 | Katsu | ............. | A43D 1/025 33/512 |
| 2006/0245091 A1 | 11/2006 | DeFazio | | |
| 2007/0225578 A1 * | 9/2007 | Howell | ............. | A61B 5/01 600/306 |
| 2008/0114269 A1 * | 5/2008 | Martindale | ............. | A61B 5/1036 600/592 |
| 2010/0076346 A1 * | 3/2010 | Abel | ............. | A61F 5/0127 600/592 |
| 2010/0179450 A1 * | 7/2010 | Abdullah | ............. | A61B 5/1036 600/587 |
| 2012/0053490 A1 * | 3/2012 | Smith | ............. | A61B 5/0082 600/592 |
| 2013/0044859 A1 * | 2/2013 | Yabugami | ............. | A61B 6/4441 378/62 |

* cited by examiner

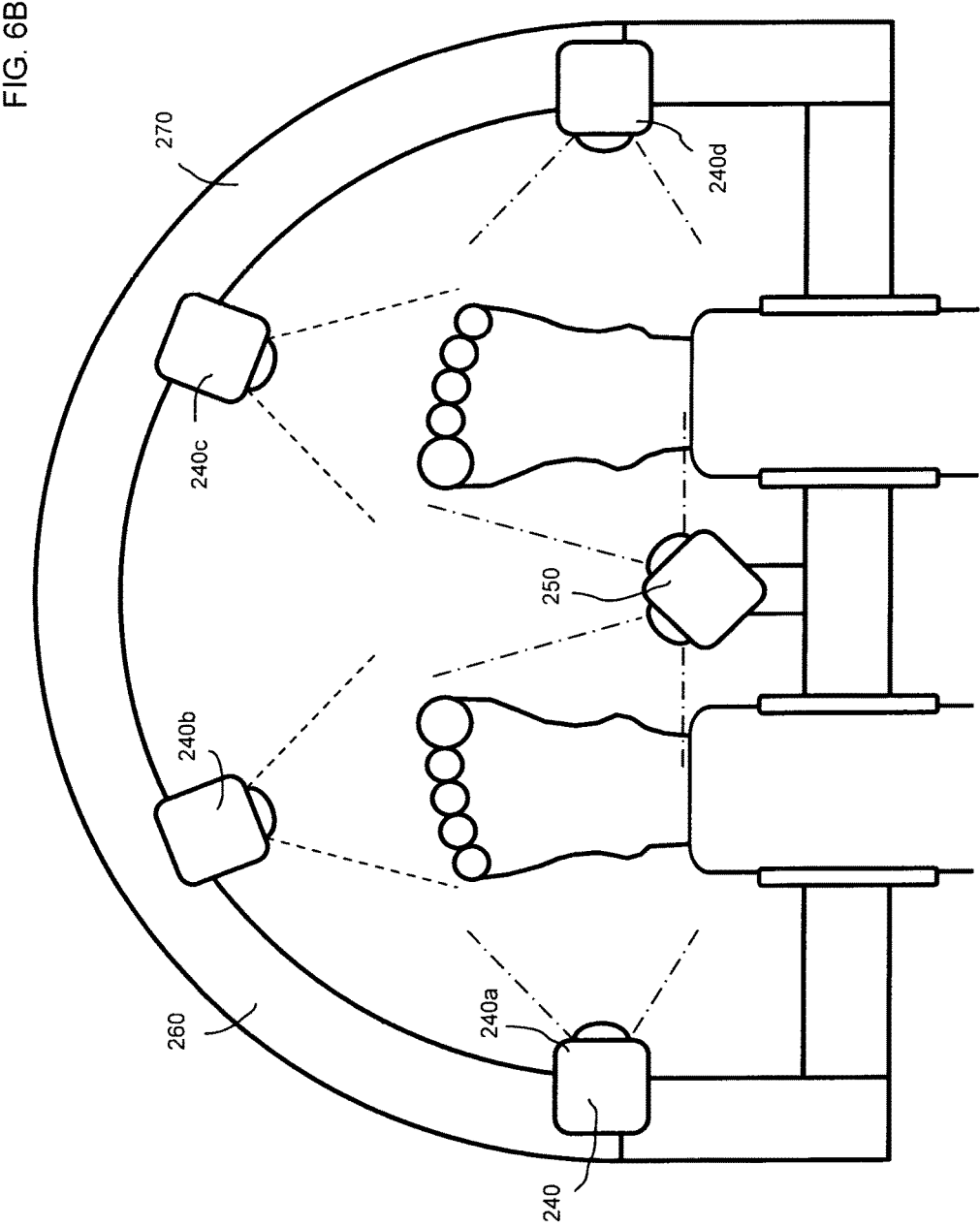

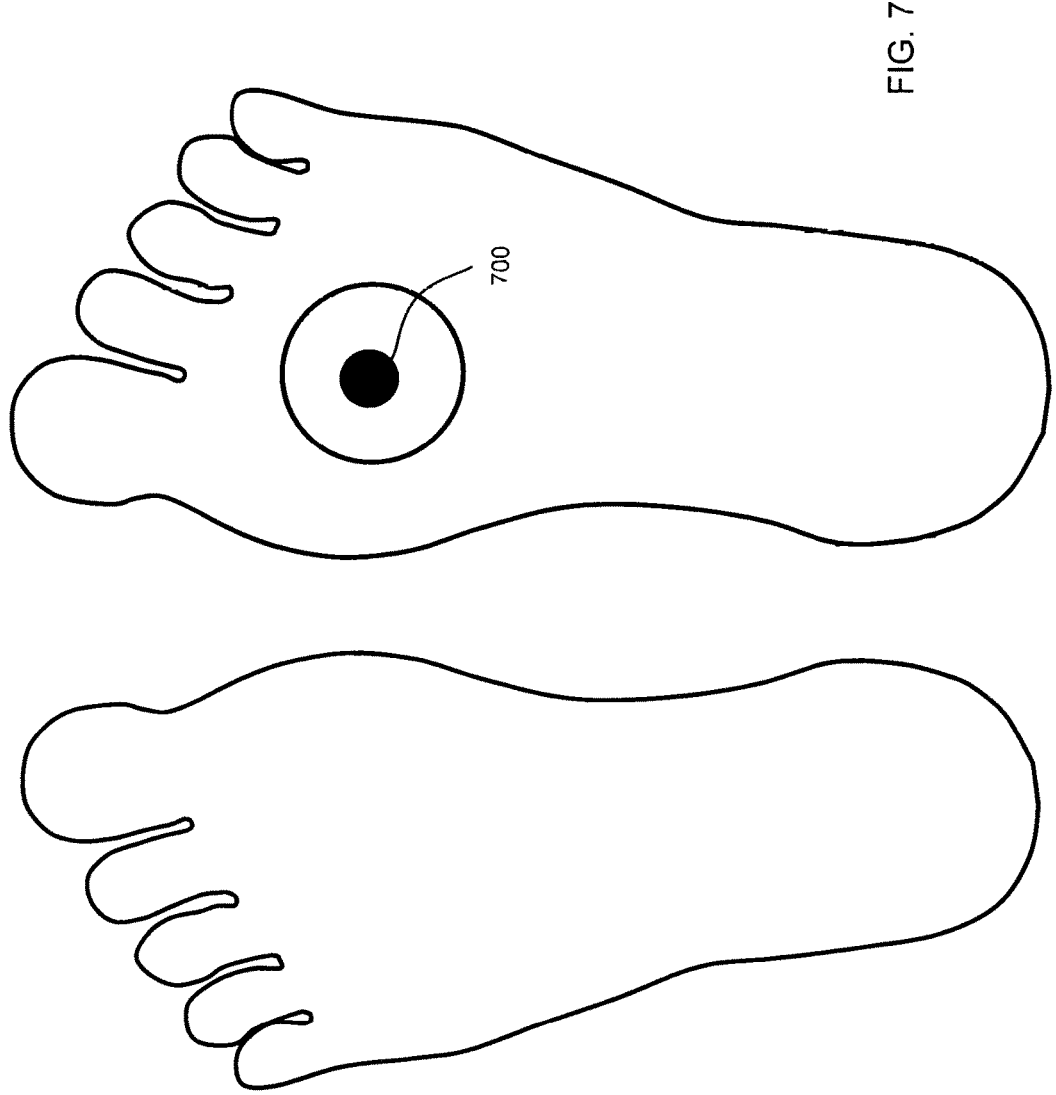

SYSTEM FOR SCREENING SKIN CONDITION FOR TISSUE DAMAGE

CROSS-REFERENCE TO RELATED APPLICATIONS

The present invention claims priority to U.S. non-provisional patent application Ser. No. 14/644,045, filed on Oct. 3, 2012, which in turn claims priority from U.S. provisional Patent Application No. 61/551,589, filed on Oct. 26, 2011, the contents of which are each hereby incorporated by reference in the entirety.

FIELD OF THE INVENTION

The present invention relates to medical device technologies. More particularly, but not exclusively, the present invention relates to portable, mobile device-implemented systems to perform screening of tissue damage to patient skin surfaces.

DESCRIPTION

Field of the Invention

The present invention relates to a novel approach to improving the use of foot screening for diabetics by offering a system for screening the skin condition of the plantar surface of the feet.

BACKGROUND OF THE INVENTION

Diabetics and other related types of diseased patients often suffer from sores, ulcers, and other symptoms of diseases that affect extremities such as the foot and other areas of the human body. Such patients often have loss of sensation, limited mobility, and decreased vision, all of which impairs their ability to monitor the condition of the skin using current technologies, especially on parts of the body that are hard to reach or view, but also on more accessible areas, such as the plantar surfaces of their feet. As such, preventing ulcers, sores and the like, or catching the presence of the same early can improve treatment outcomes and reduce the need for extreme interventions, such as amputations, thereby both resulting in improved quality of life of patients and reduced medical costs.

Heretofore, approaches for evaluating the bottom of the feet for persons at risk of tissue breakdown have been limited in various ways. One known approach relates to the provision of a small mirror (approximate 3 inches in diameter) on the end of a long handle which would be used by the patient to inspect the bottom of their foot for indications of skin breakdown, whereupon they would call their podiatrist and schedule an appointment for a physical examination. However, this system does not offer a medical provider with images, such that any assessment is made without the aid of a professional review, something which is especially problematic for someone with limited vision (e.g., especially from, say, diabetic retinopathy) given that such persons cannot readily discern the smaller, earlier signs of tissue breakdown. A similar system might involve use of a digital camera on the end of a flexible handle to aid in visualizing one's own skin for signs of pressure sores, and could possibly be made to send images to clinicians for telemedical evaluation or screening. Such a system, however, has several drawbacks, including the need for the camera and feet to remain stable during imaging.

A more advanced system has been developed in the Netherlands whereby users can image the soles of their feet, use a digital camera to image the soles of both feet, and automatically transmit the images to clinicians for evaluation. The system is contained within a box that reduces background light and uses LEDs to illuminate the feet for consistent lighting. This system, in addition to being expensive (and therefore being unlikely to receive extensive distribution as a home screening tool) utilizes horizontal bars for situation of the feet during picture acquisition, and these bars partially obstruct the full view of the feet. Furthermore, this system does not appear to show the image to the patient.

Other types of foot and skin screening for diabetics are known in the art and often take the form of simple systems wherein a user can have pictures or the like taken of his feet while in a standing position. One such approach involves a system that allows patients to stand on a glass platform that scans an image of the plantar surface of the feet and provides this image of the same. The major drawback of this system is that the plantar tissues are pressed against the glass, thereby producing artifacts that can be misinterpreted as callous tissue, or which obscures the visualization of the earliest signs of skin breakdown (e.g. redness).

It is therefore, unknown in the art to provide a system for foot and other skin screening for diabetics where the user does not stand, or otherwise have his feet or other skin surface area compressed against a support structure or platen. It is therefore a further problem in the art to provide screening method that does not compromise the image of the foot or other skin surface by compression on the skin, or in a foot, the plantar surface thereof, thereby leading to artifacts or other distortions that will be present on the image of the plantar surface as a result of such compression. It is a further problem to provide a system that offers portable home screening that can interface electronically for telemedicine approaches without the need of personal assistance or extensive equipment. It is yet another problem in the prior art to provide a system that offers real time feedback to a user of the image being taken, so that he can review the results personally and also ensure that a treating physician can receive optimized images remotely, prior to transmission thereof. It is further a problem that none of the previous systems allows clear and direct visualization of the sides (inner and outer) of the feet, which are very common sites of damage.

SUMMARY OF THE INVENTION

From the foregoing, it is seen that it is a problem in the art to provide a device meeting the above requirements. According to the present invention, a device is provided which meets the aforementioned requirements and needs in the prior art by providing unobstructed and artifact-free images of the hard to view skin surfaces, such as the feet, backside, etc., for both the patient and his clinician to view.

The proposed invention therefore relates to a novel approach to improving the treatment of diabetics and other patients who may suffer from sores, ulcers, and other symptoms of diseases that affect extremities such as the foot and elsewhere. To this end, the present invention provides for the following beneficial advances relating to: (1) Provision of a screening method that does not compromise the image of the foot by compression on skin surfaces such as posterior, the plantar surface of the foot, etc., thereby avoiding artifacts or other distortions that will be present on the image of the plantar surface as a result of such compression; (2) Provision of a screening method that offers portable home screening that can interface electronically for telemedicine approaches; (3) Provision of a screening method that offers real time feedback to a user of the image being taken, so that he can review the results personally and also ensure that a treating physician can receive optimized images remotely, prior to transmission thereof. To this end, the present invention overcomes the aforementioned and other disadvantages inherent in the prior art. Other objects and advantages of the present invention will be more readily apparent from the following detailed description when read in conjunction with the accompanying drawings.

BRIEF DESCRIPTION OF THE DRAWINGS

FIG. 6B is an overhead view of a portion of the legs, as well as the feet, of a subject utilizing one embodiment of the invention, with individual fields of photographic capture illustrated from different angles, utilizing a mobility track imaging solution;

FIG. 7 is an illustrative depiction of a thermal imaging of a subject foot that may be done as an overlay with, or independent of, a photographic still image;

DETAILED DESCRIPTION OF THE INVENTION

Figure 1A:
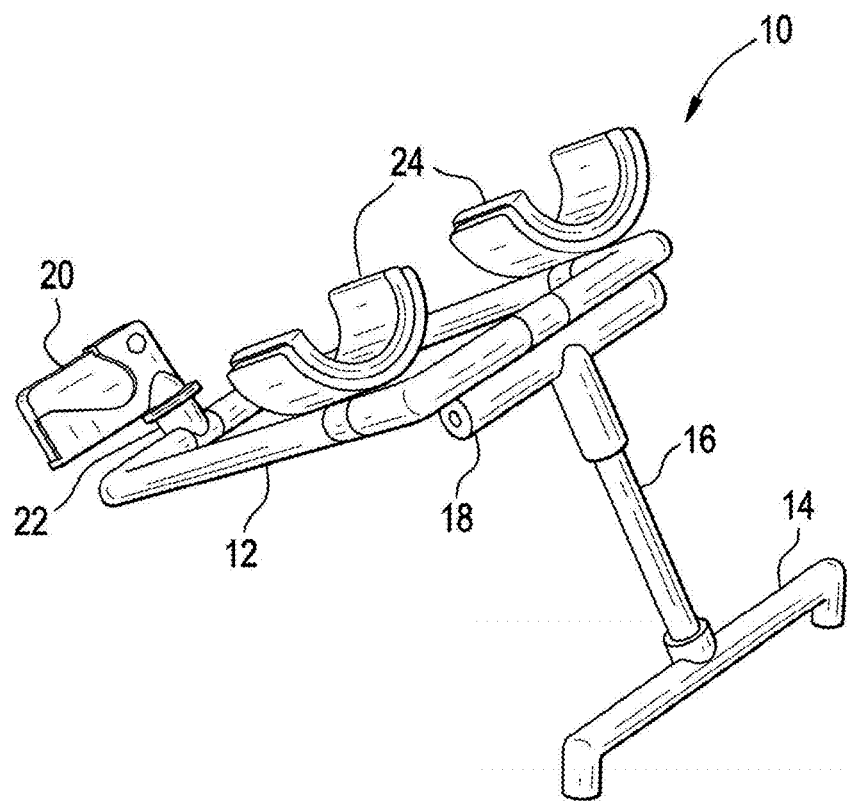
FIG. 1A is an offset elevated view of the system for screening the skin condition of the plantar surface of the feet according to the present invention.

The inventive purpose of the invention is to provide a means of screening various skin surfaces on the human body, such as the foot and areas that may be hard to reach and/or view, such as the posterior and elsewhere, where the skin condition of patients is at risk for tissue breakdown (e.g. persons with diabetes). This inventive screening approach is accomplished through the provision of a remote screening device that can be used in telemedicine or home self-monitoring approaches that can offer a solution that assists in the preventive monitoring and screening of patient skin surfaces (feet or elsewhere). In addition, the apparatus is designed to be of a low enough cost so as to facilitate, in an economic fashion, the provision of such devices to all patients at risk for skin breakdown. The invention would be operated in the home where it would record high resolution images of the bottom of the patient's feet and other areas of high risk skin areas that typically experience tissue breakdown. These images could immediately be viewed by the patient and/or electronically submitted to a medical facility where clinicians could screen the images for signs of tissue breakdown. Frequent preventive checks using this device could therefore improve the rate of early detection of tissue breakdown and could potentially improve treatment outcomes and reduce the overall occurrence of severe interventions such as amputations and the like.

At its broadest level, the present invention is directed to a system for screening the skin condition of the various skin surfaces of the human body, which in one embodiment may be directed to the plantar surface of the feet comprising: a support frame having a front portion, a rear portion, a left portion, a right portion, a top portion, and a bottom portion; a lower extremity support structure affixed to the support frame, so as to extend upwardly from the top portion of the support frame; and an image acquisition device interface affixed to the support frame, proximate to the rear portion of said support frame, the image acquisition device interface comprising retention framework for reception of, and stable retention of, an image acquisition device. In certain specific embodiments, the system for screening the skin condition of the plantar surface of the feet according the support frame may further include: (i) an elevation support framework for securely elevating said support frame substantially off a ground surface, either a static elevation stand or a foldable elevation stand hingably attached to the support frame at said front portion of said support frame; (ii) a lower extremity support structure that comprises two substantially parallel stabilizing leg cuffs; (iii) the retention framework for reception of, and stable retention of, an image acquisition device provides for the accommodation of said image acquisition device wherein the image acquisition device can be chosen from the group comprising cameras, camera-enabled smart phones, camera-enabled PDAs, and camera-enabled tablets; (iv) the support frame being at least partially formed from at least one lightweight material that is chosen from the group comprising aluminum, titanium, fiberglass, or plastic; (v) a directed illumination source and a remote trigger for triggering the image acquisition device and/or (vi) a monitor interface electronically connected to the image acquisition device for real time viewing of images acquired by said image acquisition device by an immediate user, whereby the monitor interface can, in one possible embodiment, be independently situated or alternatively, is affixed to the support frame so as to extend therefrom in an outwardly projected fashion for real time viewing of images acquired by said image acquisition device by an immediate user.

To this end, the inventive system for screening the skin condition of the plantar surface of the feet has additional features which further make it advantageous for patients when compared with conventional screening systems, in that it is portable and easily used at a home based setting, interfaces with many popular electronic devices such as laptops, iPads®, tablet PCs, PDAs, smart phones, cell phones and the like. Provision of such offers the advantage of not requiring physical situation in a clinical setting, and can limit personal visits by a patient for the purpose of ongoing screenings. To this end, the present invention overcomes the aforementioned and other disadvantages inherent in the prior art.

One embodiment would be a component in a formalized telemedicine system, prescribed by the podiatrist or other doctor for persons particularly at risk for skin problems on the feet. This type of system would involve a central platform with peripheral devices to monitor specific patient needs, and this inventive embodiment would therefore be a peripheral device for one or more of such telemedicine platforms. A different embodiment would entail instantiation as a stand-alone self-screening tool, and would accordingly be a less expensive version that could be designed using a simple digital camera with LEDs for directed illumination and a remote trigger with a basic display, such as the kind used by digital picture frames. The user could turn the system on, and then take a picture and it would immediately display on the provided hardware. One variant of this and other embodiments could also allow for simultaneous videoconferencing with the clinician using the built-in camera capabilities of say, an iPad®. or other electronic device. Other variants could cover the spectrum in between the two aforementioned embodiments. For example, the present inventive system might contemplate the inclusion of a dedicated hardware platform capable of independent transmission via the internet through either a wireless phone data plan, or through wireless internet would provide the telemedicine capability without requiring the use of a particular telemedicine platform.

Another embodiment might contemplate provision of a means of interfacing with an advanced mobile phone, so as to use the unit as both the imaging device and the means of transmission. An alternative approach to visualizing the feet would be to send the image to the user's own computer, enabling him to use a larger monitor to display a larger image. The use of real-time streaming images would allow the user to shift their feet to better visualize any questionable irregularities. In yet another alternative embodiment, provision of multiple image acquisition devices (e.g., cameras, video cameras, webcams) could permit the use of lower resolution cameras, with each focused on one foot from a closer distance, effectively obtaining higher overall resolution, without significantly increasing cost. The user could then switch between images of each foot, or could stitch the images together into a single composite image so as to permit visualization of both feet on one screen. The use of a tablet hardware platform (such as the aforementioned iPad®) would permit easy zooming, which would be particularly useful for persons with reduced vision. As an alternative, large simple buttons on a touch screen of the electronically connected monitor could act in a similar manner.

Figure 1B:
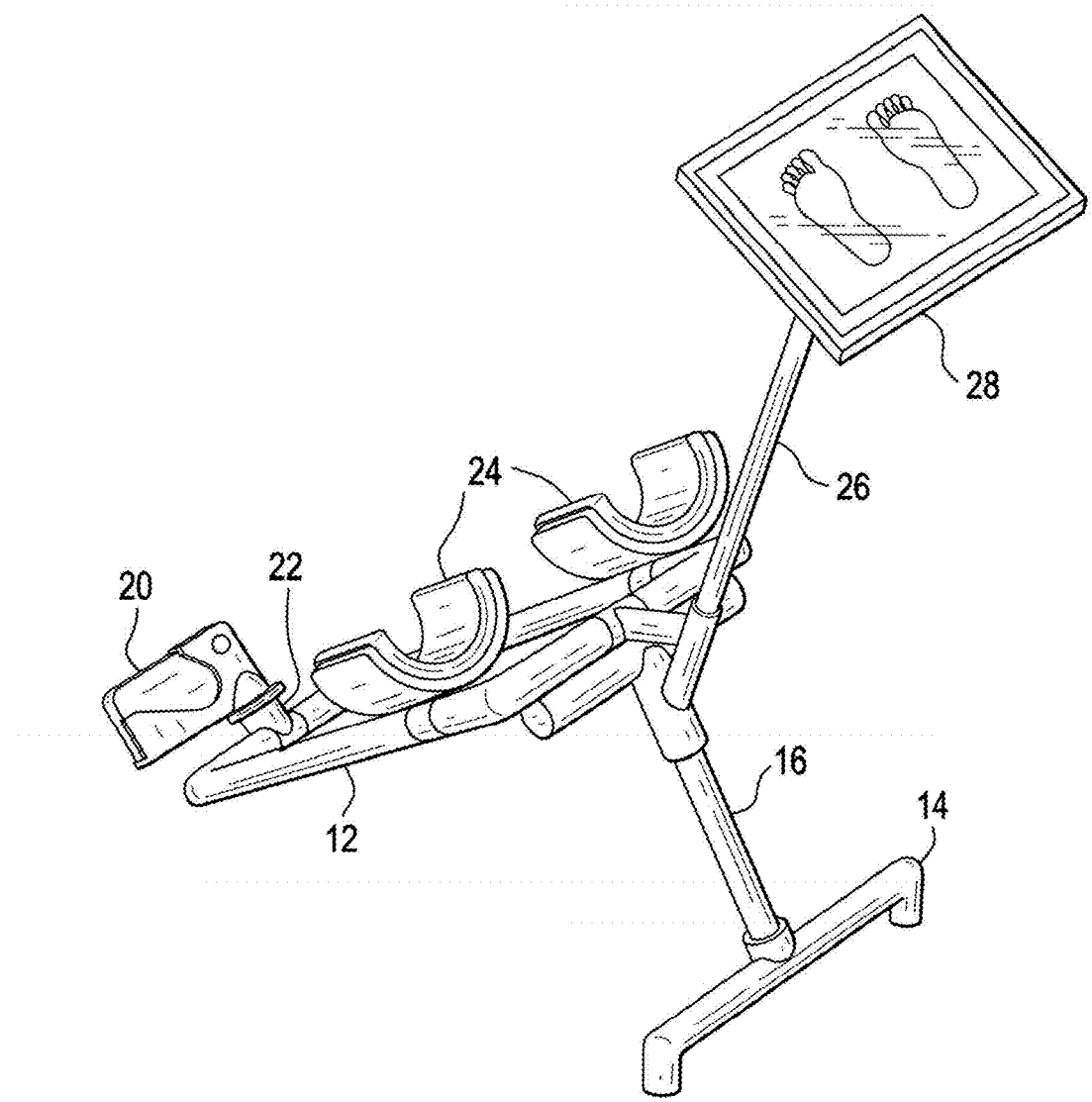
FIG. 1B is an offset elevated view of the system for screening the skin condition of the plantar surface of the feet according to the present invention with an optional monitor interface built thereon.
Figure 2:
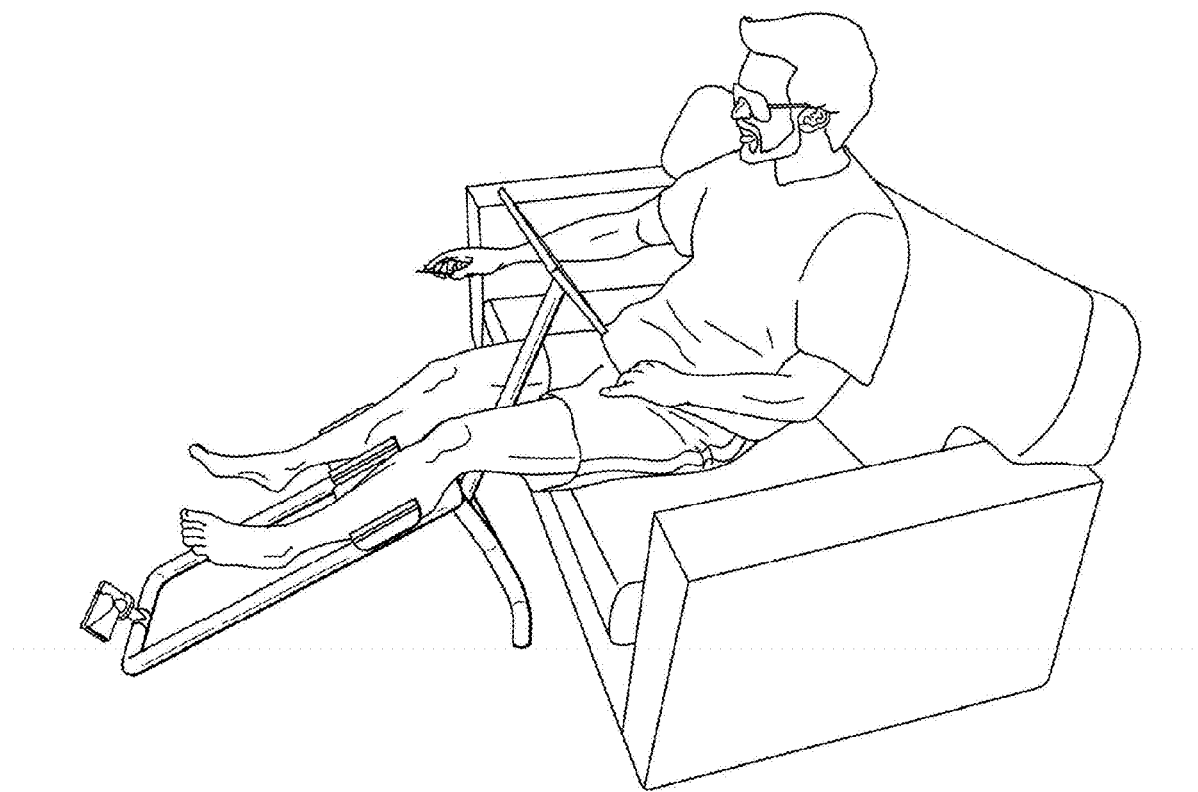
FIG. 2 is an offset elevated view of the system for screening the skin condition of the plantar surface of the feet according to the present invention with an optional monitor interface built thereon, and a user illustratively employing the same in a seated position from a chair during said usage.
Figure 3:
FIG. 3 is an offset elevated view of the system for screening the skin condition of the plantar surface of the feet according to the present invention with the aid of an electronic viewing device, such as a computer with a monitor or the like connected thereto, thereby eliminating the need for the aforementioned built in optional monitor interface of FIGS. 1B and 2, and a user illustratively employing the same in a seated position from a chair during said usage.

Thus, as seen in FIGS. 1A and 1B, and in figures described hereafter, each of the components of the present invention are more specifically discussed in greater detail below. In providing the above, the inventive system for screening the skin condition of the plantar surface of the feet 10 is therefore structured through the use of support frame 12 with lower extremity support structure 24 that supports the legs and feet of the user. Support frame 12 may have an elevation support framework 14, 16 for securely elevating said support frame substantially off a ground surface. Note that elevation support framework 14, 16 may be either a static elevation stand (not depicted, but may comprise fixed legs or walls) or as depicted, can be a foldable elevation stand hingably attached 18 to support frame 12 at the front portion of support frame 12. In either case, it can, like support frame 12, be at least partially formed from at least one lightweight material that is chosen from the group comprising aluminum, titanium, fiberglass, or high strength plastic. Lower extremity support structure 24 may be affixed on support frame 12 so as to extend in a generally upward fashion so as to support a user's lower extremities in an elevated fashion over support frame 12. As depicted, lower extremity support structure 24 may comprise two substantially parallel stabilizing leg cuffs, but as can be appreciate, alternative structures may also be employed with similar results, as long as the correct amount of overall stabilization is provided so that any images taken of the feet are not blurred from user movement, but in one embodiment, parallel stabilizing leg cuffs support the legs of the user closer to the ankles, because support of the legs closer to the ankle area (rather than on say, the calf area) situates image acquisition device 20 at a farther distance from the bottom of the user's feet which is some embodiments, can offer a more appropriate, stable position for the photographs or videos to be taken. Lower extremity support structure 24 is critical inasmuch as they support not only the lower legs, but also fully support or elevate the feet of a seated user on support frame 12 (use in the seated position is more generally depicted in FIGS. 2 and 3). Such a feature is important because it avoids the common weak points of known systems that acquire images from feet that have their plantar surfaces compressed on platens or other support structures, thereby leading to artifacts and other distortions in images. Opposite Lower extremity supports 24 is image acquisition device 20, which is normally a digital imaging device such as the camera or camera-enabled devices as described above, that are used to collect images of the plantar surface of the user's feet which, are therefore situated so that when cooperatively affixed a distance from the support of a user's legs from lower extremity support structure 24, will necessarily avoid artifacts or other distortions that would otherwise be present on the image of the plantar surface as a result of such compression. To that end, retention framework 22 is provided for the reception of, and stable (preferably elevated) retention of image acquisition device 20. To this end, retention framework 22 must provide for the accommodation of various types of possible image acquisition device 20, such as cameras, video cameras, webcams, video and/or camera-enabled smart phones, video and/or camera-enabled PDAs, and video and/or camera-enabled tablets and the like. Accordingly, this structure should ideally have a frame or slotted holding structure (not depicted) that can easily accommodate a user sliding or fitting a camera, smart phone, etc. into the frame thereof.

In one embodiment, a directed illumination source (not depicted) and a remote trigger (also not depicted) for triggering the image acquisition device may be provided. Illumination may be provided by ambient light and supplemented by directional LEDs (or other illumination sources). In an alternative embodiment of the present invention, provision may also be made for any images taken by image acquisition device 20 to be transported in either a wired fashion or via a USB port, or wirelessly via Bluetooth® or other wireless protocol, to a monitor interface 28 that is electronically connected to the image acquisition device for real time viewing of images acquired by said image acquisition device by an immediate user. As specifically seen in FIG. 1A and as depicted in use in FIG. 3, monitor interface 28 may be independently situated and may comprise any viewing device, whether a computer, smart television screen, PDA, iPad®, etc. so long as the native software therein would allow the user to see his own feet on an easily visible screen, and which is connected to image acquisition device 20 through either a wired or wireless connection. Alternatively, monitor interface 28 may be optionally affixed to support frame 12 by optional monitor interface support 26, so as to extend therefrom in an outwardly projected fashion (as depicted in FIG. 1B and as depicted in use in FIG. 2), and may comprise any viewing device, whether a computer, smart television screen, PDA, iPad®, etc., so long as the native software therein would allow the user to see his own feet on an easily visible screen. Provision of either variant such ensures that a user can start the self-screening process and can send only quality images given the ability to retake images if needed, and further ensures that the patient or user can always choose which images to send to their health care provider. To this end, either approach to provision of monitor interface 28 ensures that any images acquired by image acquisition device 20 are instantly available for viewing by an immediate user, such as the patient employing the system on his feet. Once chosen, the native software on any of the above mentioned devices will permit the user to send the target images to their doctor via secure methods over the internet or cell phone networks for the doctor's review thereof. When provided as such, should abnormalities become apparent in the images, the users are able to contact their healthcare provider and obtain the appropriate clinical care. Accordingly, as a screening tool, the device is therefore intended to indicate the need for review of the patient's feet by clinicians, thereby prompting patients to physically visit the clinic so that clinicians can address sores before they require extreme treatments.

The device also includes other approaches, such as those outlined in US Pat. Pub. No. 2005/0097762, titled "Device and Method for Examining a Diabetic Foot" and EP Pat. No. 1490651, titled "Compact Optical Contour Digitizer" and related U.S. Pat. No. 7,068,379, titled "Compact Optical Contour Digitizer", each of which are hereby incorporated by reference in their entirety.

One alternative embodiment may be described at its broadest in terms of a system for screening the skin for tissue damage, including the screening the skin condition of hard-to-view body parts, such as the buttocks, back, and the plantar surface of the feet comprising the following: (i) a support frame having a front portion, a rear portion, a left portion, a right portion, a top portion, and a bottom portion; and (ii) a retention framework for reception of, and stable retention of, at least one image acquisition device, the at least one image acquisition device thereby being situated apart from (iii) an optional lower extremity support structure so as to acquire images without artifacts or other distortions; and (iv) optional provision for a reflective-based multiple field imaging solution affixed to the support frame, proximate to the front portion of said support frame. A similar, yet different version of the above may be described as having the same or similar support frame and retention framework, but with a mobility track imaging solution affixed to the support frame, proximate to the front portion of the support frame. In any of the disclosed embodiments, the image acquisition device is situated with said retention framework so as to be "separate from any other structure" of the system for screening skin for tissue damage. The importance and meaning of this inventive aspect is that known systems cannot acquire images without artifacts or other distortions because of necessary contact with certain structural components, such as platens or stabilizing platforms. By contrast, the present invention, as illustratively depicted in the related embodiments found earlier in the present specification in the particulars pertaining to FIGS. 2 and 3, the image acquisition device is held stably in one place by the retention framework, and also, any subject human body parts having suspected tissue damage are also held stably, all without situating the same together with, or in contact with, other structure such as platens, stabilizing platforms, support frames, etc.

Figure 10:
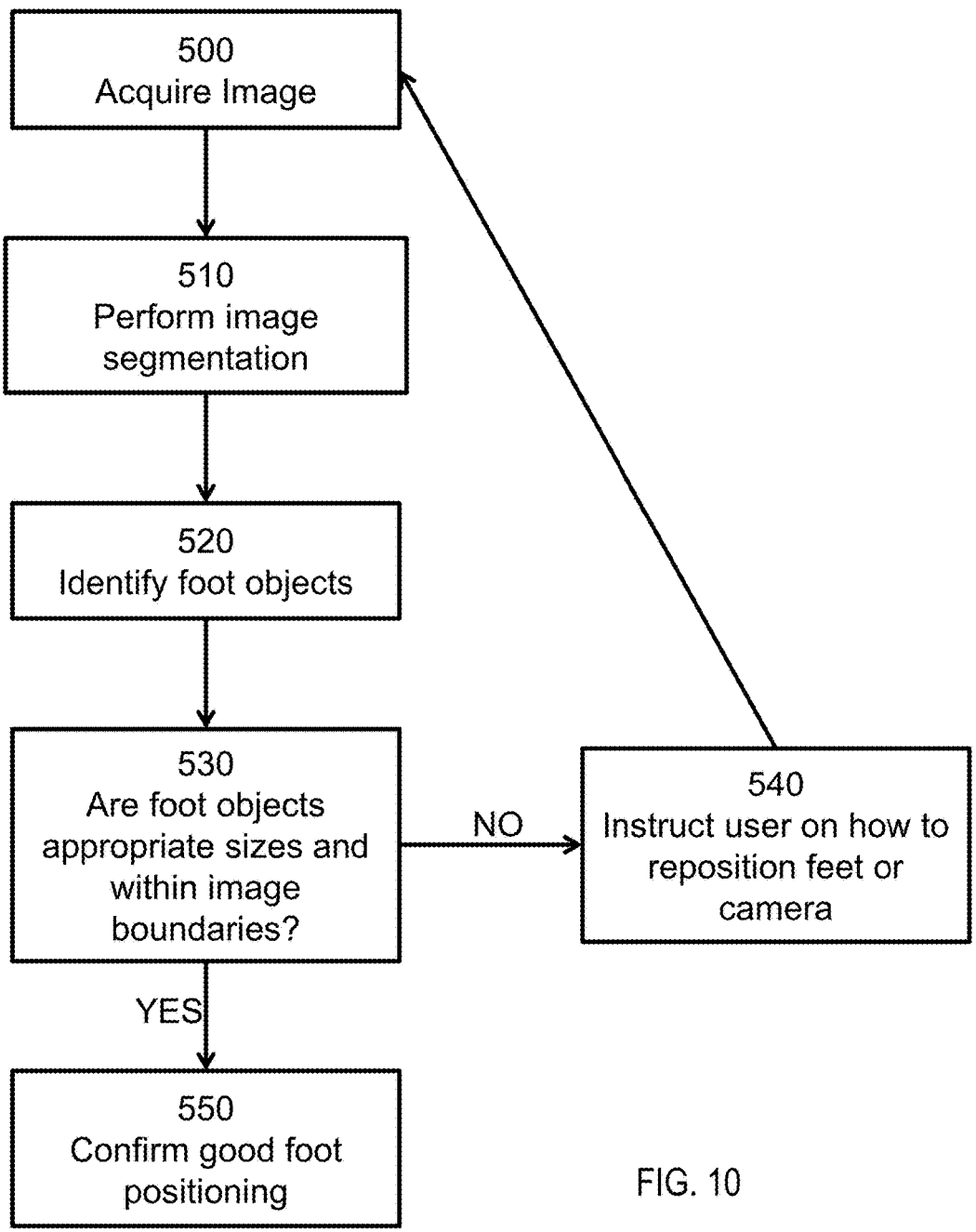
FIG. 10 is an illustrative flow diagram of the software based module that directs the image acquisition of the camera(s).

The aforementioned system may further comprise a software based image acquisition module which, among other things, executes the steps according to FIG. 10, triangulates and interpolates overlaid images and 3-D constructs, and furthermore, comprises the above-referenced image acquisition device can be at least one of the following chosen from the group comprising: a thermal imager, IR imager, a photographic still image camera, or a dual use thermal/photographic still image camera, either singly or in tandem; wherein the image acquisition devices output at least one of the following images chosen from the group comprising: thermal images, IR images, near IR images, or photographic still images, viewable independently or together as an overlay composite image. Additionally, optional provision is further made for the following which are described in greater detail hereafter: a 3-D rendering module; a change documentation module; an extendable portable stabilizer pole; and/or a flexible extending structure having a flexible member.

Figure 4:
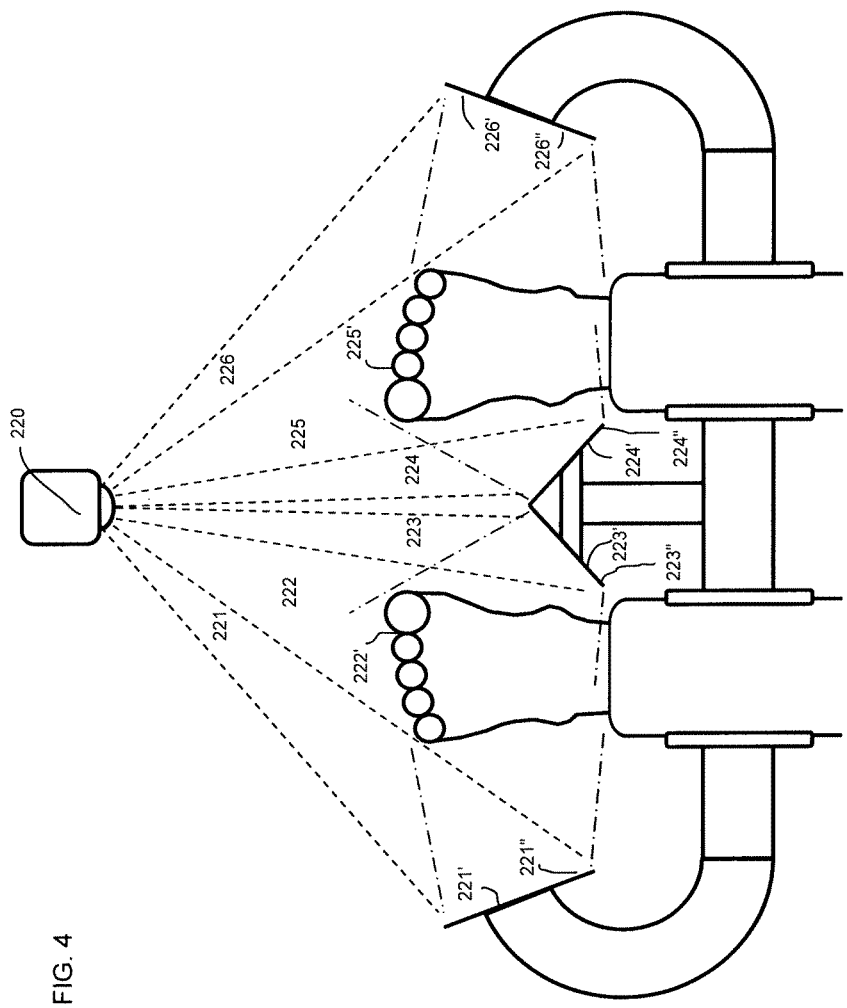
FIG. 4 is an overhead view of a portion of the legs, as well as the feet, of a subject utilizing one embodiment of the invention, with individual fields of photographic capture illustrated from different angles, utilizing a reflective-based multiple field imaging solution.
Figure 5:
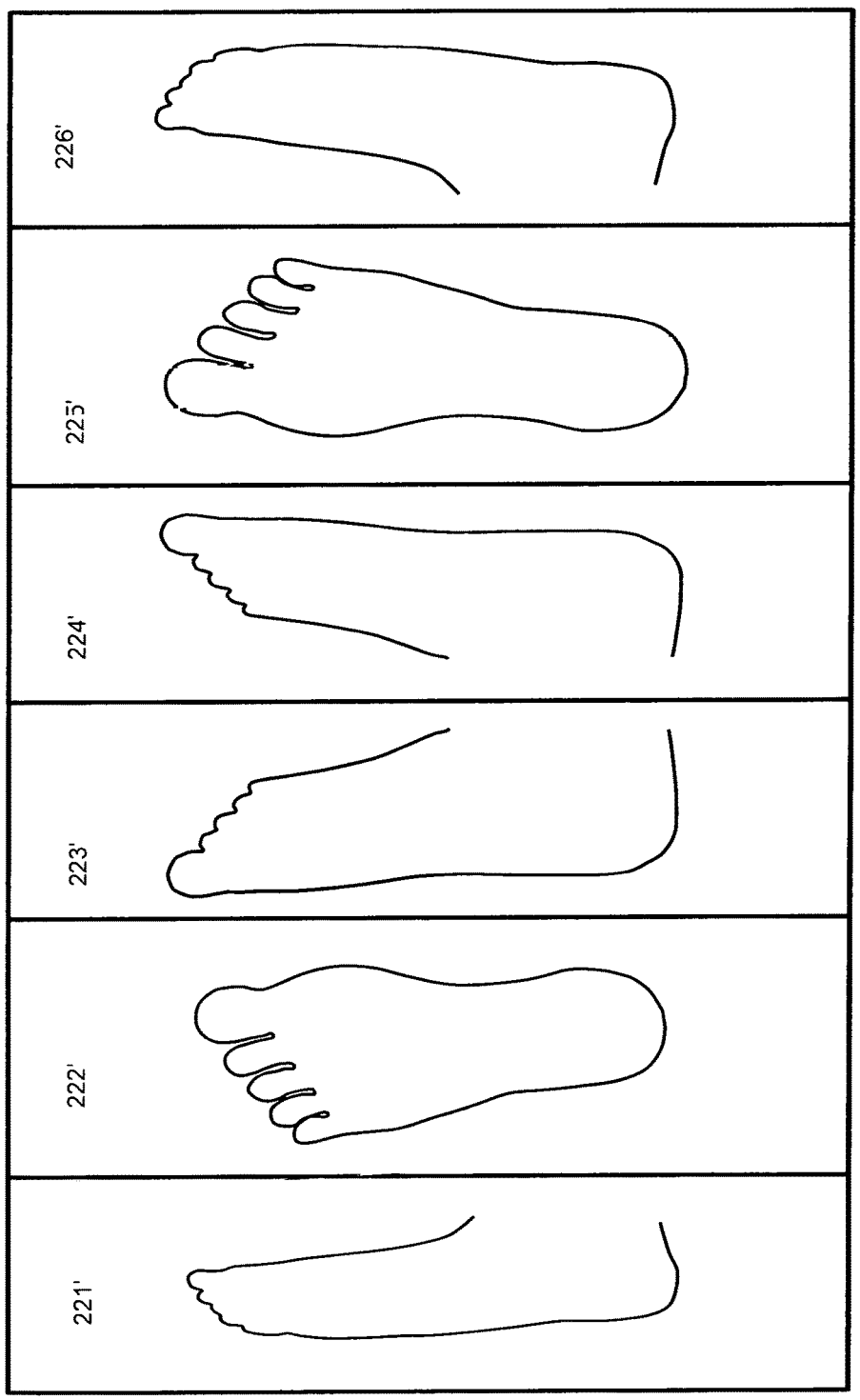
FIG. 5 indicates illustrative renditions of profile photos of the feet of a subject, from images obtained from the above-referenced reflective-based multiple field imaging solution.

In the above-described embodiment, the present invention includes particulars as described heretofore, as well as hereafter, with initial reference to FIG. 4. As seen in FIG. 4, camera 220 (either mobile device based or otherwise dedicated photographic device) is situated in one embodiment as a stationary fixture with a field of exposure that has variable sectors of image capture, referred to herein as a reflective-based multiple field imaging solution. The field of exposure may be in the range of 15°-180° of exposure, with individual segments of capture ranging from 15°-60°. The exact measurement within each of the above ranges can be adjusted based upon such variable factors such as camera resolution, distance from lens to photograph surface/subject, optimal focal area, camera resolution, etc. Thus, illustratively camera 220 may have, for example, individual segments of capture 221, 222, 223, 224, 225, 226, each of which are capturing reflected respective images 221', 222', 223', 224', 225', 226', some of which are reflected off of respective mirrored surfaces 221", 223", 224", 226". FIG. 5 indicates illustrative renditions of profile photos of the feet of a subject, from images 221', 222', 223', 224', 225', 226'. The profile photos shown in FIG. 5 allow the patient and clinician to view the plantar surfaces of the feet (222', 225'), the medial surfaces of the feet (223', 224'), and the lateral surfaces of the feet (221', 226'). Other camera and mirror configurations could also allow for views of the dorsal, anterior, and posterior surfaces of the feet.

Figure 6A:
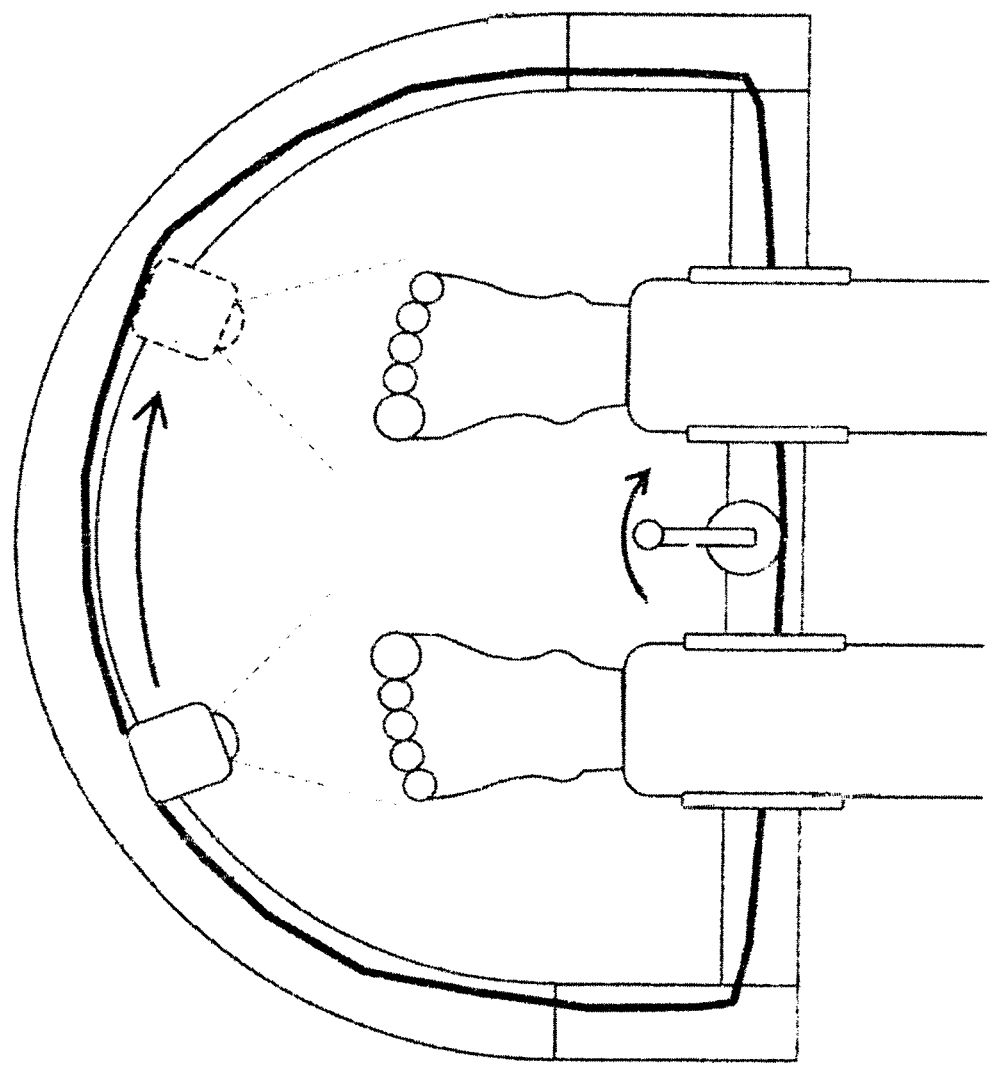
FIG. 6A is an overhead view of a portion of the legs, as well as the feet, of a subject utilizing one embodiment of the invention, a mobility track imaging solution, different angles, utilizing a cable-driven system with turn-crank.

Alternatively, FIGS. 6A and 6B indicate in one embodiment, the present invention includes particulars as described herein. As seen therefore in FIG. 6B, camera 240 (either mobile device based or otherwise dedicated photographic device) is situated in one embodiment as a mobile (e.g., physically movable) fixture that can rotate around at any predefined waypoints about a semicircular track 270, depicted illustratively as waypoints 240a, 240b, 240c, and 240d. Each defined waypoint is a point on semicircular track 270 that offers a field of exposure from each respective vantage point, wherein each respective vantage point has fields of exposure for image capture. Contrasted with the above-referenced reflective-based multiple field imaging solution, this approach is referred to as a mobility track imaging solution, and is distinct from the previous embodiment in that, in one embodiment, does not employ reflective surfaces, but instead relies upon the mobility of camera 240, together with the stationary, rotating camera 250 to provide cooperative angles of view or vantage points in order to yield renditions of profile photos of the feet of a subject, similar to images 221', 222', 223', 224', 225', 226' indicated in FIG. 5. The field of exposure of either camera 240 and/or 250 may be in the range of 15°-90° of exposure in one illustrative embodiment. Similar to the reflective-based multiple field imaging solution, the exact measurement within each of the above ranges can be adjusted based upon such variable factors such as camera resolution, distance from lens to photograph surface/subject, optimal focal area, camera resolution, etc. In order to move camera 240 along the aforementioned various waypoints in the mobility track imaging solution, a user may employ the following illustrative approaches to moving the camera long track 270, as seen in FIG. 6A: cable-driven system with turn-crank 225, in which rotating crank 225 to the right pulls, via cable 223, camera 240 in at least one illustrative direction (depicted here to the right) along track 270 and rotating crank 225 to the left pulls camera 240 to the left along the track. Another approach to move the camera would be the use of a motor to drive crank 225 rotation, with use of remote-control to drive the system along track 270. Yet another embodiment involves the use of several cameras statically positioned at different points along track 270 (as further referenced above in regards to FIG. 6B), with a system to integrate the photos for viewing by the patient and clinicians. When provided with either or all of the above, a 3-D representation module transforms photos taken from various viewing angles (viewpoints) may also be used with software to create a three-dimensional visualization of the foot by combining and interpolating surface representational data from at least three, and more preferably six angles of view (medial, lateral, posterior, plantar and dorsal) to render a 3-D output that can be viewed and in turn, rotated on a user to screen to view the overall extent and location of tissue damage. Techniques for rendering such 3-D output can be done according to known software techniques for converting planar images into 3-D representations. Alternatively, in one embodiment the process for converting such images into 3-D representations, may involve utilizing stock CAD/CAM images of a normal foot, taking the illustrative six angles of view (medial, lateral, posterior, plantar and dorsal, each of which is categorized according to previously assigned tags indicating the same during image capture), and then applying the respective images on each of the correct angles of view as described above using triangulation and interpolation techniques.

The present invention also provide for the thermal imaging of a subject foot, as illustratively indicated in FIG. 7. In one embodiment, either a thermal imager or a photographic still image camera may be used, either singly or in tandem, or alternatively, a dual use thermal/photographic still image camera may be employed that can capture thermal imaging independently or together as an overlay with a photographic still image. The benefits of the photographic still image and the thermal imaging are distinct, but nevertheless complementary. Photographic still images, especially those which are free of artifacts such as those that present themselves from feet being pressed against platens and other surfaces, are useful representation of discoloration that typically evidences sores and other injuries. On the other hand, such discoloration may, in some patients, be indicated only at certain stages, and may not be present in early stages or in evidencing sub-dermal or internal manifestations of tissue damage and the like.

To that end, thermal imaging, especially combined with the above photographic still images (whether independently viewed from each other, or whether overlaid as a visual composite) may alert medical providers to conditions that are not visible to the naked eye because the thermal imagers contemplated herein are sensitive enough to capture microspots or highly localized presentation based upon variation of temperature patterning across a given foot profile and/or an adjacent foot profile.

Two such examples of thermal imagers are microbolometer-based thermal camera and/or a plurality of infrared thermometers. An exemplary dual use thermal/photographic still image camera is available from FLIR Inc, of Wilsonville, Oreg., which can produce separate thermal images and photographic still images or can combine the images using Multi Spectral Dynamic Imaging (MSX) or picture-in-picture technology. For example, tests using the innovative thermal imaging cameras reveal that a foot is expected to be within ±4° F. of adjacent foot areas portions. Thus, if the thermal imaging indicated a variance greater than this illustrative range, then tissue damage is indicated in the area of the foot that is coextensive with the anomalous thermal reading portion, whether topically, or sub-dermally. It is noted that in this particular embodiment where the thermal imaging is combined with photographic still imagery, the innovative process is herein termed a bimodal overlay, and effectively results in a complementary sensory process check. A complementary sensory process check is an innovative means to ensuring that neither the thermal imaging, nor the photographic still imagery yield false positives. When used independently, the thermal imaging can yield a false positive from natural, yet perfectly harmless dermal irregularities such as calluses (which tend to show distinctly different surface temperature when compared with surrounding tissue), which, in a bimodal overlay photographic still imagery, would show that the initially alarming temperature difference is simply indicated in the photo to be normal callusing. Conversely, photographic still imagery can yield false positives by similarly harmless anomalies, such as lint, etc., which, depending on variables such as camera resolution, lint coloring, etc., could initially alarm a practitioner into believing that tissue damage existed, when in fact none was present. It would only be through the provision of the bimodal overly that the thermal imaging would show the lint as a false positive because no significant temperature difference would exist at the spot of lint occlusion. Thus, the bimodal overlay is a complementary, two-way process check that yields vastly superior rates of error free telemedicine diagnosis.

Some related technologies exist for thermal imaging, and alternatively, for photographic still imagery of tissue damage. Such systems may include, for example, "Three-dimensional thermal imaging for the detection of skin lesions and other natural and abnormal conditions", U.S. Pat. No. 8,923, 954, Filed Jul. 12, 2011, Herman, C., and "Methods and apparatus for imaging, detecting, and monitoring surficial and subdermal inflammation", US Pat. Applic. No. 2013/0162796, filed Oct. 13, 2011, Bharara, M. et al., "Medical image projection and tracking system", US Pat. Applic. No. 2012/0078088, filed Mar. 29, 2012, Whitestone, J., the disclosures of which are hereby incorporated by reference in their entirety. However, while these systems may offer additional details for one skilled in the art regarding thermal imaging and photography particulars, they not only lack many of the additional novel points detailed herein, but given their size and complexity, they lack portability, as well as utility in telemedicine and self-diagnosis applications. Additionally, they do not provide for the non-contact assessment of surface areas as detailed throughout the present application, given that these systems detail the use of weight bearing platforms, platens, etc., and do not offer stabilization structures of the present invention, and lastly, require extensive equipment and/or third parties to assess the same.

When provisioned above, the system can also provide for a change documentation module. Essentially the change documentation module comprises at least a date and time stamping of all images, and a systematic tagging of the view classification (illustratively, where applicable, according to a medial surface tag, a lateral surface tag, a dorsal surface tag, an anterior surface tag, a posterior surface tag), all of which can be archived for later referral by viewers, who can easily view changes in any given surface area of the foot, across any given increment of time (or even across all times, including as a rapid view that simulates time elapsed video progression of changes to the various surfaces) in order to review changes relating to location and extent of tissue damage and/or tissue healing.

Figure 8:
FIG. 8 is an offset side view of an illustrative embodiment of an innovative combined photographic and thermal imaging foot surface rendition according to the usage of the same through a dual use thermal/photographic image camera, with an extendable portable stabilizer pole.

As described above, the still image camera and/or thermal imager can be utilized in any one of the cameras described above, whether cameras 220, 240, or 250. Any one of these camera can alternatively be employed on a more portable frame, as illustratively depicted in FIG. 8. FIG. 8 shows an illustrative embodiment of an innovative combined photographic and thermal imaging foot surface rendition according to the usage of the same through a dual use thermal/photographic image camera, with an extendable portable stabilizer pole. Although not depicted, the extendable (and therefore retractable) stabilizer pole 800 may have an optional stabilization member for situating the same against a lower surface 820. Note that the camera 830, when attached pole 800, may transmit, wirelessly or otherwise, to a remote screen or mobile device which serves as a viewer 810.

Figure 9:
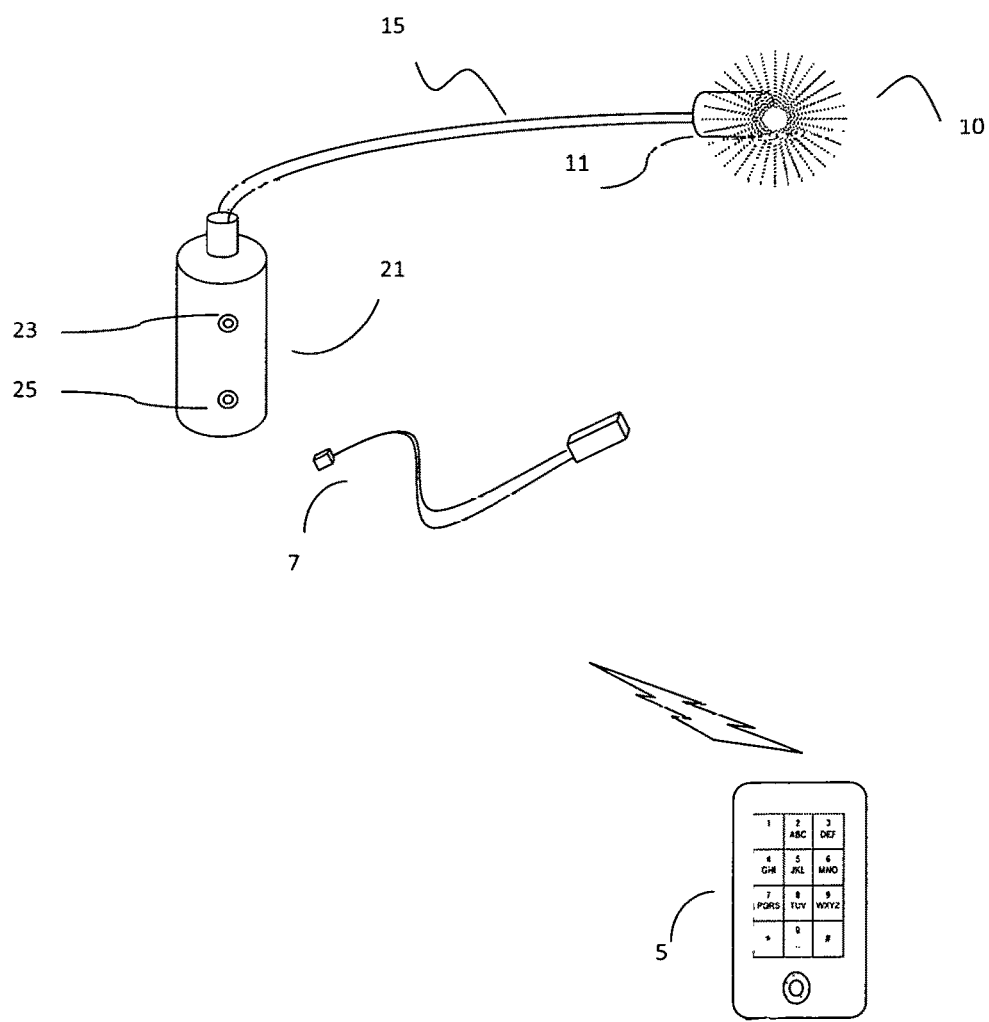
FIG. 9 is an illustrative depiction of a portable, flexible dual use thermal/photographic image camera, and optional connective mobile device setup.

In yet another alternative embodiment, FIG. 9 is an illustrative depiction of a portable, flexible single type or dual use thermal/photographic image camera (e.g., as in cameras 220, 240, or 250, described above), and optional connective mobile device setup. The purpose of this flexible extending structure embodiment is for portable, lightweight, flexible angling of a camera, in order to provide access to portions of the body that are not normally accessible by a solo user. In this embodiment, a camera 10 is illustratively miniaturized for purposes of balance and weight, optionally connected via a connector 11 to flexible member 15, which in turn connects via optional connecter 21 to user handle 20. Flexible member 15 may be provided from any flexible or easily bendable material, such as plastic, metal, rubber, etc. that offers flexibility with enough stiffness to prevent the payload (e.g., camera 10) from drooping the same along whatever length of material one desires. In one alternative, flexible member 15 or another portion of the overall structure, such as an optional stabilization member or the like (not depicted), within this embodiment could be rested against the side of a user's body while laying on one's side to create a stable image of the posterior of the body, or alternatively, an optional bracket attachment may be utilized. Provided on user handle 20 are illustrative effectuating buttons, such as capture button 23 and illumination button 25. The handle has provision for wired 7, or wireless (not depicted) transmission to a remote screen or mobile device 5. Provision of such, whether camera 10 entails thermal and/or photographic still imaging (or alternatively, video) offers the user, and remotely located medical providers the option to more effectively assess tissue damage, such as diabetic ulcers located on the back, posterior or other hard-to-access portions of the human body.

Turning attention now to FIG. 10, an illustrative flow diagram depicts some of the processes underlying the software based image acquisition module that directs the image acquisition of the camera(s). This software based module may reside within any camera described herein, or may be resident within an electronic device connected thereto. In any case, as seen in FIG. 10, step 500 indicates that camera 220, 240, etc. acquire image, perform image segmentation 510 by dividing the image into regions that correspond to different objects using appropriate computer vision algorithms (e.g., histogram-based, watershed, or edge-detection algorithms), then identify foot objects 520 among the regions in the image using appropriate computer vision algorithms (e.g., template, edge, or histogram matching, blob analysis, or the Viola-Jones object detection algorithm), and then, decide whether foot objects are appropriate sizes and are within image boundaries at step 530, such that if they are not, step 540 mandates instruction to user regarding how to re-position feet and/or camera and begin anew the acquisition image step 500, and alternatively, once the feet are properly positioned, confirm the final foot positions at step 550. Thereafter, optional steps (not depicted in FIG. 10) may indicate the need for thermal imaging in addition, or instead of, still image traditional photography, and additionally, whether to overlay the two types as indicated above.

The invention being thus described, it will be evident that the same may be varied in many ways. Such variations are not to be regarded as a departure from the spirit and scope of the invention and all such modifications are intended to be included within the scope of the claims.

We claim:

1. A system for screening skin for tissue damage comprising:
    a support frame structure;
    at least one image acquisition device;
    a retention framework structure for reception of, and stable retention of, said at least one image acquisition device, said retention framework attached to said support frame structure, wherein:
    said at least one image acquisition device is situated with said retention framework so as to be separate from any other structure of said system for screening skin for tissue damage, so as to acquire images without artifacts or other distortions.

2. The system for screening skin for tissue damage of claim 1 further comprising a reflective-based multiple field imaging solution affixed to said support frame structure.

3. A system for screening skin for tissue damage comprising:
    a support frame structure;

a mobility track imaging solution structure having at least one image acquisition device, said mobility track imaging solution being affixed to said support frame structure;

a retention framework structure for reception of, and stable retention of, said at least one image acquisition device, said retention framework structure being affixed to said mobility track imaging solution structure wherein:

said at least one image acquisition device is situated with said retention framework structure so as to be separate from any other structure of said system for screening skin for tissue damage, so as to acquire images without artifacts or other distortions.

4. The system for screening skin for tissue damage of claim 1 or 3, said system further comprising a change documentation module.

5. The system for screening skin for tissue damage of claim 4, wherein said image acquisition device is chosen from the group comprising:

a thermal imager, IR imager, a photographic still image camera, or a dual use thermal/photographic still image camera, either singly or in tandem;

said image acquisition devices outputting at least one of the following images chosen from the group comprising:

thermal images, IR images, or photographic still images, viewable independently or together as an overlay composite image.

6. The system for screening skin for tissue damage of claim 5, said system further comprising a 3-D rendering module.

7. The system for screening skin for tissue damage of claim 5, said system further comprising a software based image acquisition module, and includes a bimodal overlay.

8. The system for screening skin for tissue damage of claims 1 or 3, wherein said image acquisition device is chosen from the group comprising:

a thermal imager, IR imager, a photographic still image camera, or a dual use thermal/photographic still image camera, either singly or in tandem;

said image acquisition devices outputting at least one of the following images chosen from the group comprising:

thermal images, IR images, or photographic still images, viewable independently or together as an overlay composite image.

9. The system for screening skin for tissue damage of claim 8, said system further comprising a 3-D rendering module.

10. The system for screening skin for tissue damage of claim 8, said system further comprising a software based image acquisition module, and includes a bimodal overlay.

11. The system for screening skin for tissue damage of claims 1 or 3, wherein said support frame structure comprises an extendable portable stabilizer pole.

12. The system for screening skin for tissue damage of claims 1 or 3, wherein said support frame structure comprises a flexible extending structure having a flexible member.

* * * * *